(12) United States Patent
Chien et al.

(10) Patent No.: US 11,854,678 B2
(45) Date of Patent: Dec. 26, 2023

(54) SYSTEMS, METHODS, COMPOSITIONS AND DEVICES FOR PERSONALIZED NUTRITION FORMULATION AND DELIVERY SYSTEM

(71) Applicant: Hygieia Health Co., Limited, Hong Kong (HK)

(72) Inventors: Xiaoming Chien, San Ramon, CA (US); Jingshi Joe Zhou, Shanghai (CN)

(*) Notice: Subject to any disclaimer, the term of this patent is extended or adjusted under 35 U.S.C. 154(b) by 313 days.

(21) Appl. No.: 16/247,874

(22) Filed: Jan. 15, 2019

(65) Prior Publication Data
US 2019/0221299 A1 Jul. 18, 2019

Related U.S. Application Data

(60) Provisional application No. 62/617,370, filed on Jan. 15, 2018.

(51) Int. Cl.
*G16H 20/13* (2018.01)
*G07F 17/00* (2006.01)
(Continued)

(52) U.S. Cl.
CPC ............. *G16H 20/13* (2018.01); *A23L 33/00* (2016.08); *A61J 1/00* (2013.01); *B01F 33/00* (2022.01);
(Continued)

(58) Field of Classification Search
CPC .... G16H 20/13; G16H 20/60; G07F 17/0092; G07F 13/06; B01F 13/00; B01F 13/1005;
(Continued)

(56) References Cited

U.S. PATENT DOCUMENTS

| 6,330,491 B1 | 12/2001 | Lion |
| 2005/0065645 A1 | 3/2005 | Liff et al. |

(Continued)

FOREIGN PATENT DOCUMENTS

| AU | 2013244938 A1 * | 9/2014 | ............... A23L 2/52 |
| AU | 2013244938 B2 * | 6/2017 | ............ A23L 33/15 |

(Continued)

OTHER PUBLICATIONS

E. Blumberg, Jeffrey B., et al. "The Evolving Role of Multivitamin/Multimineral Supplement use among Adults in the Age of Personalized Nutrition." Nutrients 10.2 (2018) (Year: 2018).*

*Primary Examiner* — Amber A Misiaszek
(74) *Attorney, Agent, or Firm* — Dentons Davis Brown, P.C.; Matthew W. Coryell (57) ABSTRACT

The disclosed apparatus, systems and methods relate to the delivery of personalized nutraceutical products to a subject, comprising a library of actives; a software module; and a dispensing unit. In certain aspects, the system further comprises a packaging unit and a delivery unit. According to certain aspects, the library of actives comprises a plurality of active nutraceutical ingredients formulated for precise dispensing. In further aspects, the software module is constructed and arranged to receive prescription information for the subject and to output dispensing instructions to the dispensing unit. In still further aspects, the dispensing unit is constructed and arranged to receive dispensing instructions from the software module and to dispense one or more actives from the library of actives to form a nutraceutical product, and wherein the dispensing instructions are derived from the prescription information and customized to the nutritional needs of the subject.

14 Claims, 6 Drawing Sheets

(51) Int. Cl.
    *A23L 33/00*     (2016.01)
    *A61J 1/00*     (2023.01)
    *G16H 20/60*     (2018.01)
    *B01F 33/00*     (2022.01)

(52) U.S. Cl.
    CPC ......... *G07F 17/0092* (2013.01); *G16H 20/60* (2018.01)

(58) Field of Classification Search
    CPC .. B01F 13/1072; B01F 13/1066; A23L 33/00; A23L 33/10; A61J 1/00
    USPC .......................................................... 705/2–3
    See application file for complete search history.

(56) References Cited

U.S. PATENT DOCUMENTS

| | | | |
|---|---|---|---|
| 2007/0125442 A1* | 6/2007 | Tribble | A61J 3/002 141/27 |
| 2009/0011031 A1* | 1/2009 | Staniforth | A61M 15/0051 424/489 |
| 2009/0220613 A1* | 9/2009 | Odidi | A61K 9/1652 424/497 |
| 2010/0150994 A1* | 6/2010 | Kotyla | A61K 8/0291 424/490 |
| 2010/0330189 A1* | 12/2010 | Niichel | A23P 10/25 424/722 |
| 2011/0014351 A1 | 1/2011 | Reider et al. | |
| 2011/0195157 A1* | 8/2011 | Niichel | A61K 31/522 426/74 |
| 2011/0208153 A1* | 8/2011 | Alvey | A23L 33/12 426/71 |
| 2012/0041778 A1 | 2/2012 | Kraft | |
| 2014/0282197 A1 | 9/2014 | Keefe et al. | |
| 2016/0140288 A1* | 5/2016 | Kuan | G16B 50/00 702/19 |
| 2017/0156388 A1* | 6/2017 | Gallardo | A23L 33/185 |
| 2018/0088112 A1* | 3/2018 | Fan | C12N 15/1096 |

FOREIGN PATENT DOCUMENTS

| | | |
|---|---|---|
| CN | 106233290 A | 12/2016 |
| TW | 20135069 A | 12/2013 |
| TW | 201350069 A1 | 12/2013 |
| WO | 2017215893 A1 | 12/2017 |

\* cited by examiner

SYSTEMS, METHODS, COMPOSITIONS AND DEVICES FOR PERSONALIZED NUTRITION FORMULATION AND DELIVERY SYSTEM

CROSS-REFERENCE TO RELATED APPLICATION(S)

This application claims priority to U.S. Provisional Application No. 62/617,370 filed Jan. 15, 2018, and entitled "METHODS AND SYSTEMS FOR MANUFACTURING, PACKAGING, AND DELIVERING PERSONALIZED NUTRITION," which is hereby incorporated by reference in its entirety under 35 U.S.C. § 119(e).

TECHNICAL FIELD

The disclosed technology relates generally to personalized nutrition and in particular, to the devices, methods, and design principles allowing the delivery of personalized nutraceutical formulations with precision, tailored to individual subject health needs.

BACKGROUND

Personalized nutrition is an area of increased focus for achieving better health. While there has been much focus on tailored diets and nutrition based on different diagnostic tools, the current methods used to make personalized nutrition typically involve merely mixing up amounts of different nutrients and existing products available in the market. As a result, subjects have to consume large quantities of products in order to obtain the expected benefit. Due to the limitations of existing product offerings, subjects may end up consuming too much of certain actives and not enough in others. It is also a significant challenge to make nutrition/dietary supplement that suits each individual's need in a large scale, and to do so economically. Accordingly, most dietary supplements are made based on the needs of a population average. For individuals whose nutritional needs deviate significantly from that average, these supplements can be ineffective, or even harmful.

Thus, there is a need in the art for methods and systems to deliver nutraceuticals and supplements that are specifically tailored to individual health needs.

BRIEF SUMMARY

Disclosed herein is a system to deliver personalized nutraceutical products in precision to a subject, comprising a library of actives; a software module; and a dispensing unit. In certain aspects, the system further comprises a packaging unit and a delivery unit. According to certain aspects, the library of actives comprises a plurality of active nutraceutical ingredients formulated for precise dispensing. In further aspects, the software module is constructed and arranged to receive prescription information for the subject and to output dispensing instructions to the dispensing unit. In still further aspects, the dispensing unit is constructed and arranged to receive dispensing instructions from the software module and to dispense one or more actives from the library of actives to form a nutraceutical product, and wherein the dispensing instructions are derived from the prescription information and customized to the nutritional needs of the subject. According to still further embodiments, the packaging unit is constructed and arranged to package the nutraceutical product and wherein the nutraceutical product is packaged in sachets, bottles, jars, or tubes. In certain aspects, the delivery unit is constructed and arranged to receive delivery information from the software module and to deliver the packaged nutraceutical product to the subject.

In further aspects, the nutraceutical actives are one or more of vitamins, minerals, amino acids, herbs, botanicals, enzymes, probiotics, prebiotics, or a concentrate, metabolites, constituent, extract or combination of any of the foregoing and wherein the nutraceutical product is formulated for a specified health condition or nutritional need. In yet further aspects, the form of the nutraceutical product maybe granulated powers, tablets, capsules, or soft gels.

According to certain embodiments, each of the plurality of active ingredients has a size ranging from about 0.5 mm to about 10 mm in diameter and/or length. In further embodiments, the quantity of the one or more active is dispensed according to the weight of the one or more active. In still further embodiments, the one or more active is dispensed by counting the number(s) of the minibeads, and/or granulated power(s), tablet(s), capsule(s), and soft gel(s) of each of the one or more actives.

Further disclosed herein is a system for dispensing a personalized nutraceutical product to a subject comprising a software module constructed and arranged to receive prescription information from the subject's healthcare provider, a library of actives, comprised of a plurality of nutraceutical active ingredients, wherein each of the plurality of nutraceutical active ingredients is comprised of a plurality of minibeads, a dispensing unit constructed and arranged to receive dispensing instructions from the software module and to dispense one or more active ingredients from the library of actives, the dispensing unit comprising: a plurality of active vessels, wherein each of the plurality of active vessels houses a single active ingredient, wherein each of the plurality of active vessels is configured to dispense a quantity of the active ingredient determined by the dispensing instructions; a dispensing belt, positioned below the plurality of active vessels and configured to receive one or more active ingredients dispensed from the active vessels; and a mixing chamber, constructed and arranged to receive one or more actives from the dispensing belt and to mix the one or more active ingredients to form a nutraceutical product, a packaging unit, constructed and arranged to package the nutraceutical product; and a delivery unit, constructed and arranged to receive delivery instructions from the software module and deliver the packaged nutraceutical products to the subject.

In certain embodiments, the software module provides an interface for the health care provider to input dosage levels for each of the one or more active ingredients. In certain aspects, the quantity of each active ingredient dispensed is determined by the weight of the minibeads. In further aspects, the quantity of each active ingredient dispensed is according to the number of the minibeads.

According to certain aspects, the nutraceutical active ingredients are vitamins, minerals, amino acids, herbs, botanicals, enzymes, probiotics, prebiotics, or a concentrate, metabolites, constituent, extract or combination of any of the foregoing.

Further disclosed herein is a method of delivering a nutraceutical product to a subject in need thereof comprising: receiving prescription information from a healthcare provider of the subject via a software module; inputting dispensing instructions from the software module into a dispensing unit, wherein the dispensing unit is comprised of a plurality of active ingredient vessels, and wherein each of the active ingredient vessels houses one of a plurality of nutraceutical active ingredients, dispensing a precise quantity of the one or more of the active ingredients from the active vessels according to the dispensing instructions, mixing the one or more active ingredients in a mixing chamber to form a nutraceutical product, and packaging for the nutraceutical product for delivery to the subject. According to certain aspects, each of the plurality of nutraceutical active ingredients is comprised of a plurality of minibeads. In further aspects, the precise quantity of the one or more active ingredients is determined by the weight of the minibeads dispensed. In yet further aspects, the precise quantity of the one or more active ingredients is determined by counting of the minibeads dispensed.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to the target of administration, e.g., an animal. Thus the subject of the herein disclosed methods can be a vertebrate, such as a mammal, a fish, a bird (e.g., a goose, a chicken, or a duck), a reptile, or an amphibian. Alternatively, the subject of the herein disclosed methods can be a can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed systems and methods, the subject has been diagnosed with a need for treatment prior to the treatment step.

One object of the current disclosure is to provide a system for the dispensing a nutraceutical product that provides a personal and precision nutritional needs of an individual subject by making active components work together effective, safely and efficiently.

A further object of the current disclosure is to provide a system provide a system for the dispensing a nutraceutical product that is designed based on individual subject health status together with a consideration of each active ingredient's effect on human wellness, as well as the effect of a combination of ingredients.

A still further object of the current disclosure is to provide a system for the dispensing a nutraceutical product that provides a product based on an individual need instead of product created for a population average, which may be harmful to some individuals.

A yet further object of the current disclosure is to provide a system for the dispensing a nutraceutical product that contains each of the actives ingredients required to meet a subject's health needs, with a minimum of excipients and fillers, and allowing the subject to meet all health/nutritional needs in a single dose nutraceutical product.

The various embodiments disclosed or contemplated herein relate to systems, devices and methods for the preparation and shipping of nutritional supplements and other compositions, specifically tailored to the nutritional and/or health needs of the recipient. In certain aspects, the disclosed is a system designed for the delivery of personalized nutraceutical products in precision to a subject and the system is comprised of a library of actives comprising a plurality of active nutraceutical ingredients, formulated for precise dispensing; a software module, constructed and arranged to receive prescription information for the subject and to output dispensing instructions; a dispensing unit, constructed and arranged to receive dispensing instructions from the software module and to dispense one or more actives from the library of actives to form a nutraceutical product, wherein the dispensing instructions are derived from the prescription information and customized to the nutritional needs of the subject; a packaging unit, constructed and arranged to package the nutraceutical product; and a delivery unit, constructed and arranged to receive delivery information from the software module and to deliver the packaged nutraceutical product to the subject.

According to certain implementations, the disclosed system comprises a library of actives. In certain embodiments, the library of actives is comprised of a plurality of active nutraceutical ingredients. The active nutraceutical ingredients may comprise any composition known in the art to have properties that have a positive impact on health or nutrition, upon administration to a subject. In certain implementations, a nutraceutical ingredient may supplement a nutrient that is deficient in a subject's body. In further embodiments, an active nutraceutical ingredient may be useful in preventing, treating, or ameliorating a health condition. According to certain exemplary embodiments, individual active ingredients of the plurality of active nutraceutical ingredients, may belong generally to one or more of the following categories: vitamins, minerals, amino acids, herbs, botanicals, enzymes, probiotics, prebiotics. In further implementations, or a concentrate, metabolites, constituent, extract or combination of any of the foregoing.

According to certain embodiments, the active nutraceutical ingredients are present in a form to allow for precision dosing. As used herein, "precision dosing" means a highly accurate and reproducible dispersals of a specified quantity of a given active. In certain implementations, the dosage form of the active allows for incremental and stepwise increases or decreases in the quantity of the active dispersed. "Precisely dosing" may also refer to the highly tailored relationship between the dose of an active dispensed and the health needs of the subject.

In exemplary aspects of these implementations, the dosage form may be minibeads, granulated powers, tablets, capsules, and/or soft gels. As used herein, minibead means a substantially round, or a substantially oblong particle that is comprised of an active nutraceutical ingredient, or, that encapsulates an active nutraceutical ingredient. In implementations where the minibead encapsulates an active nutraceutical ingredient, the active ingredient may be in solid or liquid form. As will be appreciated by those skilled in the art, minibeads can take various dosage forms. By way of non-limiting example, minibeads may include, but are not limited to: minitablets, minicapsules, and minisoftgels. In certain implementations, the disclosed minibeads range in size from about 0.5 mm to about 10 mm in diameter and/or length. According to further embodiments, the minibeads range in size from about from about 1 mm to about 5 mm in diameter and/or in length. According to further embodiments, the minibeads range in size from about 3 mm to about 5 mm in diameter and/or length. While minibead size may vary from one active nutraceutical ingredient to another, minibead size for a particular active ingredient is substantially uniform. In certain implementations, minibead size for a particular active ingredient varies no more than +/−10%. In further aspects, the per-minibead dose of a given active is substantially uniform for minibeads of that particular active. As will be appreciated, the substantially uniform character of minibead size and dose for each active allows for precision dosing and incremental adjustments of dose, either up or down, according to the health needs of the subject.

In certain embodiments, the form of the nutraceutical product is controlled release. In exemplary embodiments, the active nutraceutical ingredient comprises an enteric coating. As will be appreciated by those skilled in the art multiple approached to implementing controlled or sustained release are possible.

In certain implementations, the system provides as software module that is constructed and arranged to receive prescription information for the subject for whom the nutraceutical product will be produced. In exemplary implementations, the software module is comprised of a user interface that allows the user (e.g. a health care provider) to input prescription information from which the software module derives the nutraceutical product to be dispensed. According to certain embodiments, the prescription information is a specified dosage of one or more active ingredients to be dispensed. According to certain alternative embodiments, the user inputs on or more health conditions or nutritional deficiencies and the software module presents the user with a menu of one or more actives that may be suitable to treat the specified nutritional/health need or condition. In these embodiments, the user can then from the proposed actives and further specify the dose of each of the selected actives. In certain exemplary embodiments, the users selects from a menu of software proposed doses of each proposed active ingredient.

According to certain embodiments, the system provides nutraceutical formulations for a wide variety of health conditions and/or nutritional deficiencies. Exemplary categories for which the disclosed system provides tailored nutraceutical formulations includes, but is not limited to: brain—cognitive health preservation; brain—nootropic; female health, gynecological, breast, reproductive, pre-menopausal and/or menopausal, male health, including muscle and sexual function, genitourinary, prostate and related urinary conditions; antiaging and mitochondrial health including age related muscle loss (sarcopenia), gut health, musculoskeletal joint health, musculoskeletal bone health, skin health and healing; mood and stress support; respiratory—upper/lower; neurologic, including pain/migraine, fatigue; thyroid; eye health, including macular health (e.g., prevention of macular degeneration), lens health (e.g., prevention of cataracts); sleep health; cardiovascular including cardiovascular inflammation and heart attack, stroke risk, and optimal blood pressure support; metabolic including diabetes blood sugar support; detoxification and liver support; immune support; and optimal vitamin mineral supplementation.

In exemplary embodiments, the user of the software module is an individual with sufficient expertise and knowledge of the condition of the subject to create personalized and precision nutritional formula to meet the nutrition and dietary supplement needs to the subject. In certain implementations, the user of the software module is a healthcare provider. A health care provider may include, but is not limited to, the subject's physician, health coach, nurse, dietitian, or nutritionist. According to certain alternative embodiments, the user is the subject.

In certain implementations, the prescription information provided to the software module by the user includes subject genetic information. In these implementations, the subject genetic information is used by the software module to modify proposed prescription recommendations according to an analysis of the subject genetic information. According to certain exemplary embodiments, the subject genetic information includes genetic markers that indicate whether a particular active may be suitable for a subject. In Exemplary implantations, subjects are screened for Cytochrome P450 3Ar (CYP3A4), an important enzyme implicated in most clinically significant drug-to-drug interactions, needs to be analyzed for suitability of the subject to administration of St. John's Wort. According to further implementations, subjects are screened for a genetic mutations of Methylenetetrahydrofolate Reductase (MTHFR). Particular mutations in MTHFR lead to low levels of folate and other B vitamins. In such subjects, methylated B-Vitamins are among the actives dispensed or suggested to be dispensed to the user.

In certain implementations, the prescription information includes data on levels of inflammatory biomarkers Inflammatory biomarkers may include, but are not limited to: C-reactive protein (CRP), TNFα, TNF RII, IL-β, IL-1ra/IL-1F3, IL-2, IL-4, IL-5, IL-6, IL-8, CXCL8/IL-8, IL-10, IL-12 p70, IL-17A, GM-CSF, ICAM-1, INF-gamma, MMP-8, MMP-9, VEGF and IL-12p70, neutrophils, lymphocytes and eosinophils count, neutrophil elastase activity, alpha-1-antitrypsin (AAT), haptoglobin, transferrin, an immunoglobulin, granzyme B (GZMB), eosinophil cationic protein (ECP), eotaxin, tryptase, chemokine C—C motif ligand 18 (CCL18/PARC), RANTES (CCLS), surfactant protein D (SP-D), lipopolysaccharide (LPS)-binding protein and soluble cluster of differentiation 14 (sCD14). According to further embodiments, the software module modifies the recommend active ingredients based on the presence of one or more of the foregoing marks.

According to certain embodiments, the system includes a dispensing unit constructed and arranged to receive dispensing instructions from the software module and to dispense one or more active ingredients from the library of actives. In exemplary embodiments, the dispensing unit comprises a plurality of active vessels, and each of the plurality of active vessels houses a single active ingredient. In further aspects of these embodiments, the plurality of active vessels is configured to dispense a specified quantity of the active ingredient it houses, as determined by the dispensing instructions. In certain implementations, upon receiving dispensing instructions, the active vessel dispenses the specified quantity of active ingredient onto a dispensing belt. In exemplary embodiments, the dispensing belt is positioned below the plurality of active vessels and configured to received one or more active ingredients dispensed from the active vessels. In further aspects, the dispensing unit further comprises a mixing chamber, constructed and arranged to receive one or more actives from the dispensing belt and to mix the one or more active ingredients to form a nutraceutical product.

According to certain embodiments, the one or more active is dispensed by counting the number(s) of minibeads, and/or granulated power(s), tablet(s), capsule(s), and/or soft gel(s) of each of the one or more actives. In exemplary implementations of these embodiments, each active vessel outfitted with an optical counter. As will be appreciated by one skilled in the art, other counting methods are possible.

According to certain alternative embodiments, the quantity of the one or more active is dispensed according to the weight of the one or more active.

In certain implementations, the system comprises a packaging unit. In these implementations, the packaging unit is constructed and arranged to package the nutraceutical product according to instructions provided by the software module. In exemplary implementations, the nutraceutical product is packaged in sachets, bottles, jars, or tubes.

In certain implementations, the system further comprises a delivery unit. According to certain implementations, the delivery unit is constructed and arranged to receive delivery instructions from the software module and deliver the packaged nutraceutical product to the subject.

Further disclosed herein is a method of delivering a nutraceutical product to a subject in need thereof comprising the steps of receiving prescription information from a healthcare provider of the subject via a software module; inputting dispensing instructions from the software module into a dispensing unit, wherein the dispensing unit is comprised of a plurality of active ingredient vessels, and wherein each of the active ingredient vessels houses one of a plurality of nutraceutical active ingredients; dispensing a precise quantity of the one or more of the active ingredients from the active vessels according to the dispensing instructions; mixing the one or more active ingredients in a mixing chamber to form a nutraceutical product; and packaging to the nutraceutical product for delivery to the subject.

In certain aspects, each of the plurality of nutraceutical active ingredients is comprised of a plurality of minibeads. According to certain implementations of these aspects, the precise quantity of the one or more active ingredients is determined by the weight of the minibeads dispensed. According to certain alternative embodiments, the precise quantity of the one or more active ingredients is determined by counting of the minibeads dispensed.

According to further aspects, the disclosed method further comprises packaging step. In exemplary aspects of these embodiments, the method comprises packaging the nutraceutical in sachets, bottles, jars, or tubes by inputting packaging instructions into a packaging unit from the software module.

According to yet further aspects, the disclosed method further comprises a delivery step. In these aspects, the method further comprising delivering the nutraceutical product to the subject.

Figure 1:
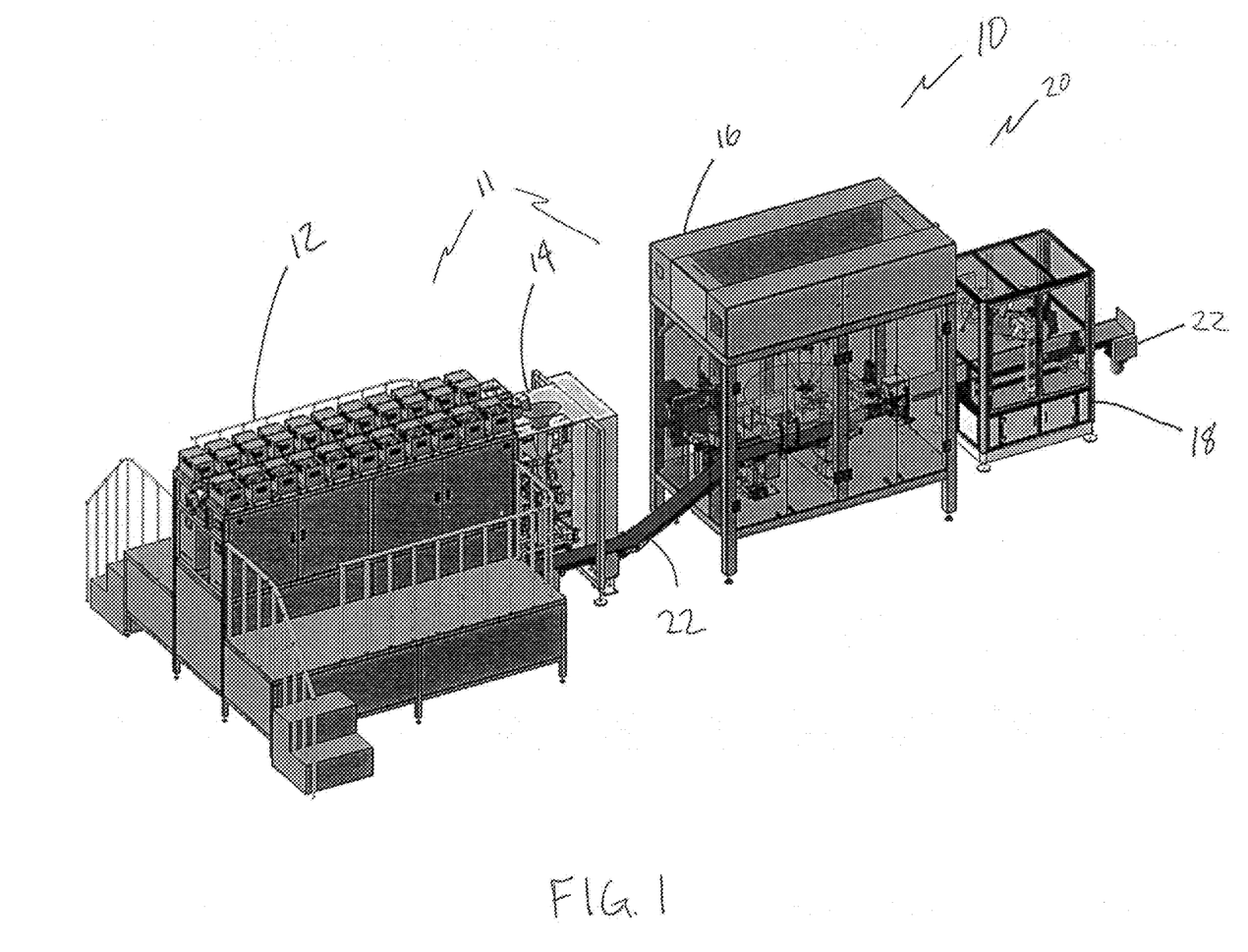
FIG. 1 is a perspective view of an exemplary nutritional system, according to one implementation.
Figure 2:
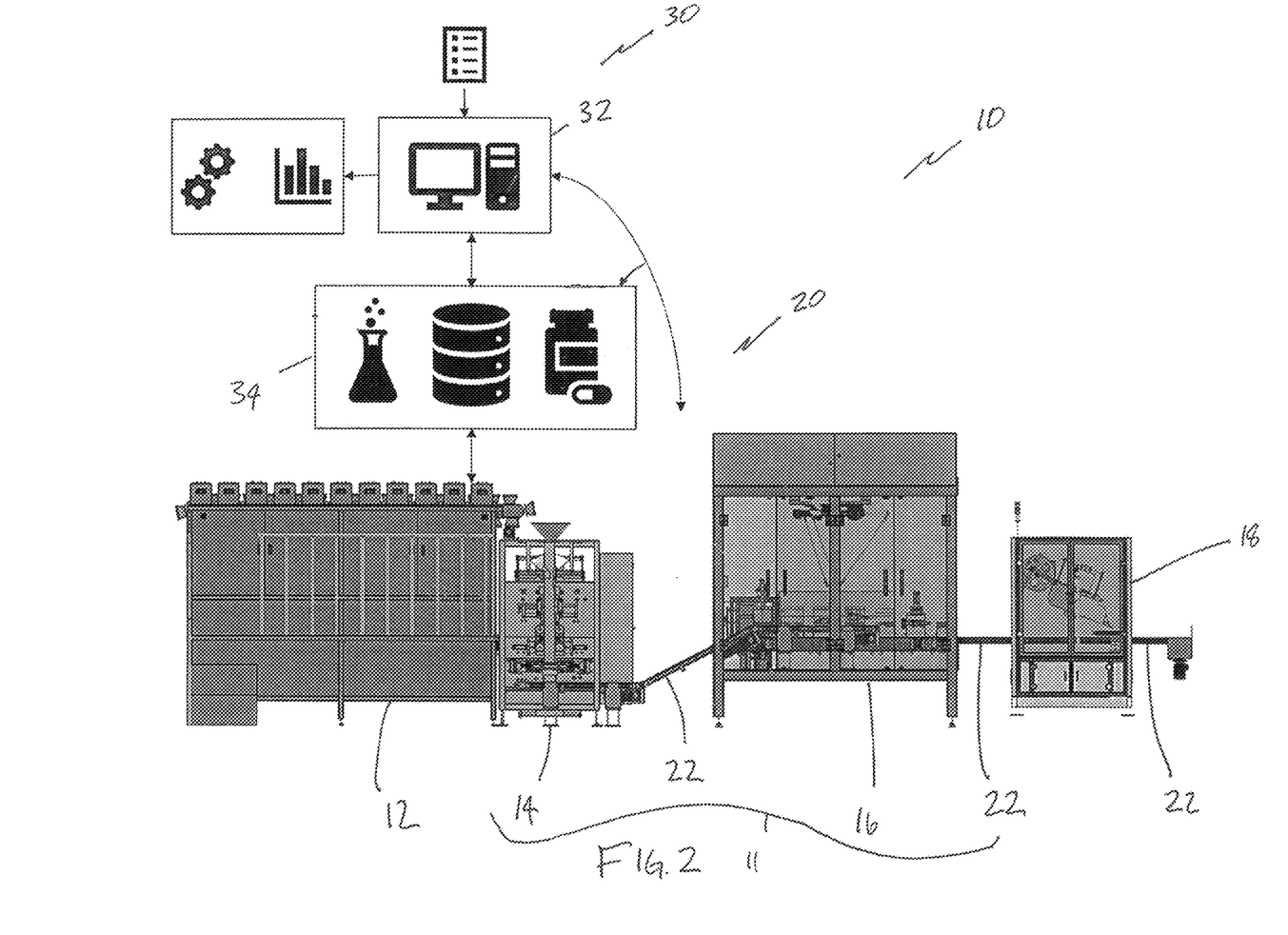
FIG. 2 is a side-view schematic of a nutritional system depicting the software module and delivery components, according to one implementation.

Turning to the drawings in greater detail, an overview of an exemplary nutrition system 10 according to one implementation is shown in FIG. 1 and FIG. 2. In this and other implementations, the system 10 comprises batching and delivery components, several optional batching and delivery components 20, such as a dispensing unit 12, a packaging unit 11 that can comprise a bagging unit 14 and/or a boxing unit 16. Certain implementations may also have a delivery unit 18. It is understood that each of these individual batching and delivery components 20 is optional in various implementations.

In these and other implementations, the various components can be in transitional communication with one another via a conveyor 22 or other mechanism for transporting dispensed active ingredients between the various modules.

As shown in the implementation of FIG. 2, the system 10 also can include an software module 30 constructed and arranged to receive prescription information for the subject and to output dispensing instructions for execution by the dispensing, packaging, and delivery components 20. In these and other implementations, the software module 30 has one or more optional networked components including an order module 32 and at least one database 34. In various implementations, the order module 32 and database 34 or databases are constructed and arranged to receive, store and transmit prescription information 36 and generate and transmit dispensing instructions to the batching and delivery components 20 for execution.

It is understood that in various implementations the database 34 may comprise several diffuse databases and can be disposed remotely from the batching and delivery components 20 or integrated within the batching and delivery components 20 or individual aspects of the database can be distributed between multiple physical locations but is operationally integrated with both the software module 30 and batching and delivery components 20 either directly or indirectly.

As shown in FIG. 2, in certain implementations, the software module 30 is constructed and arranged to receive prescription information 36 from a prescription information source, such as an order or prescription entered by a user (e.g., a health care provider).

Figure 3:
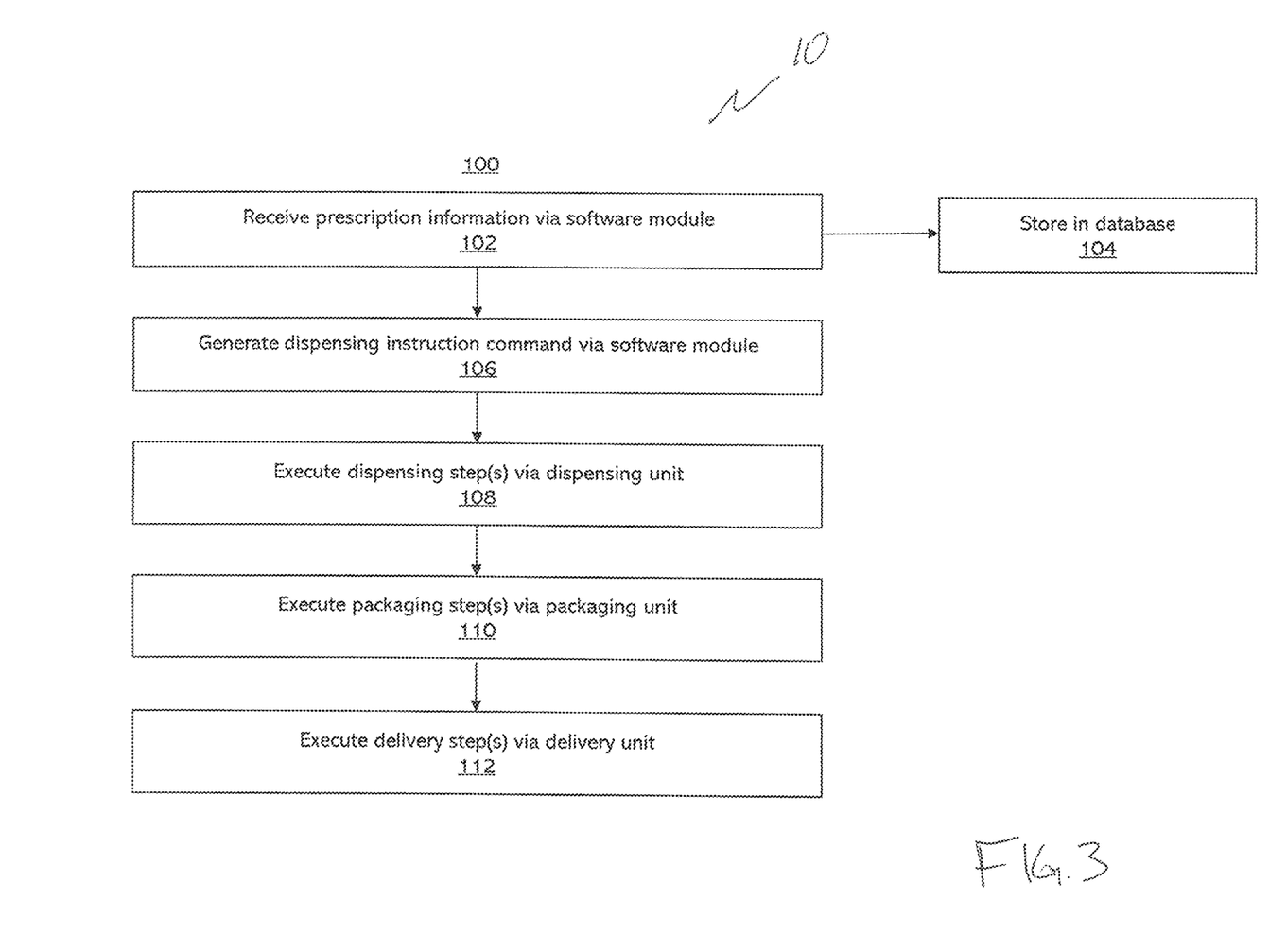
FIG. 3 is a system flowchart, depicting several optional process steps, according to one implementation.

In these and other implementations, and as shown in FIG. 2 and FIG. 3, the order module 32 may be in operational communication with a database 34 and/or the batching and delivery components 20 so as to be configured to generate dispensing instruction dispensing instructions from received prescription information 36 via a series of optional steps.

As shown in the flow chart of FIG. 3, the system 10 according to certain implementations executes a series of optional process steps 100. In one optional step, prescription information is received from a prescription information source (box 102), such as a prescribing physician or the patient, such as via the order module 32. The prescription information is used to define one or more indication. It is understood that the prescription information according to various implementations may include subject health information such as a diagnosis from the users' health care provider, lab values from blood test or other standard diagnostic testing, genetic markers of health and/or disease, user reported symptoms, family history, as well as certain standard formulation information, such as a necessary or allergic health information and order information that may include shipping information and other personal information, as would be understood.

In a further optional step shown in FIG. 3, the software module 30 transmits the prescription information to at least one database 34, where it is stored and generates dispensing instructions (box 104). It is understood that in alternate implementations, the database 34 stores a variety of indication information related to individual prescription information conditions.

In a further optional step of the implementation of FIG. 3, the software module 30 generates dispensing instructions for execution via the batching and delivery components (box 106) comprises information about the library of actives stored in the dispensing unit 12 (discussed below).

In various implementations, the software module 30 transmits dispensing instructions to the batching and delivery components 20 for dispensing and shipping.

Figure 4A:
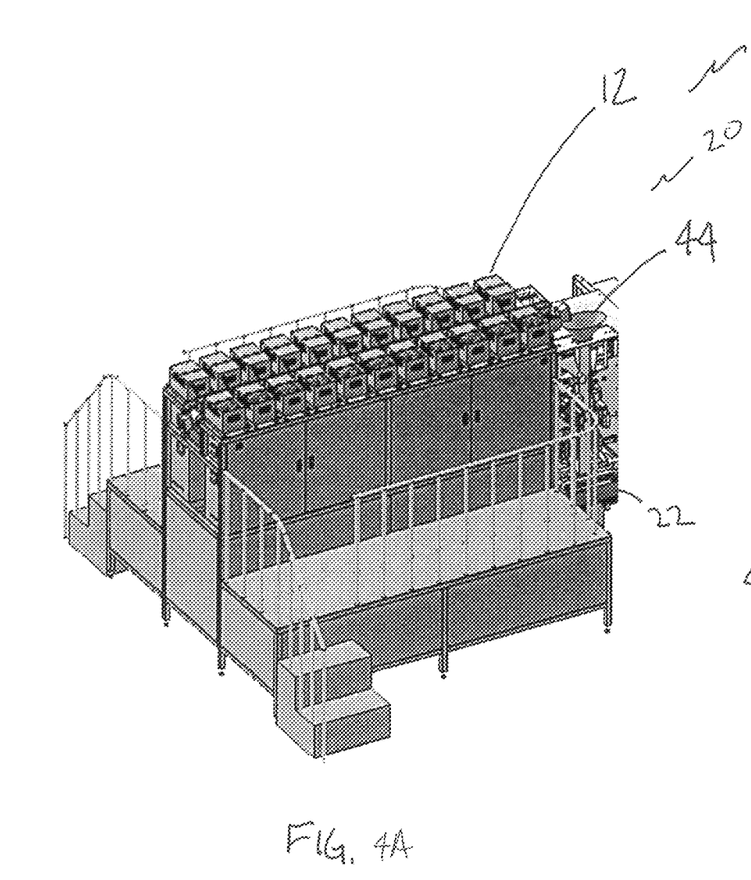
FIG. 4A is a perspective view of a dispensing unit, according to one implementation.
Figure 4B:
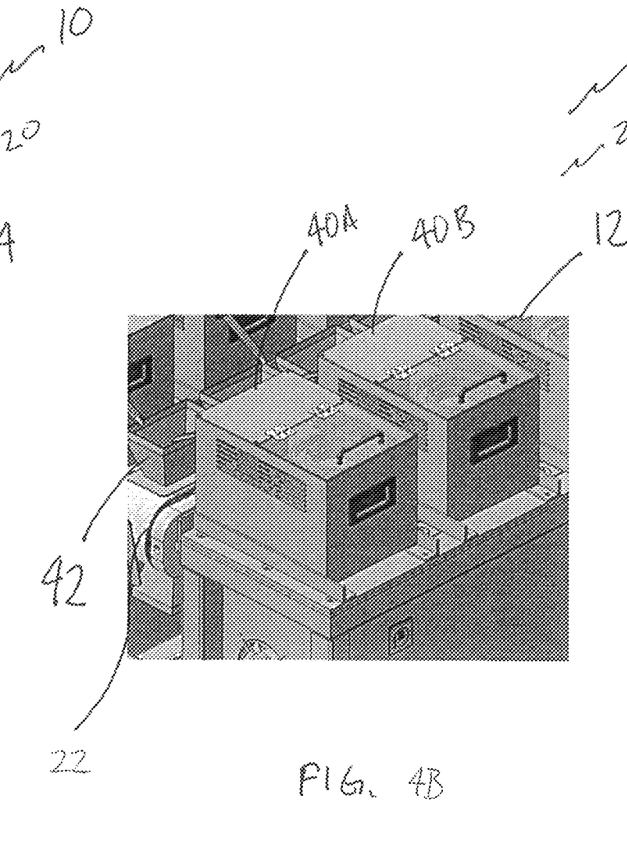
FIG. 4B is a close-up view of the dispensing unit implementation of FIG. 4A, depicting the active vessels or modular counting machines and mixing chamber.

As shown in FIG. 3, upon receipt of dispensing instructions from the software module, the dispensing unit (shown in FIG. 1 and FIG. 2 at 12) executes one or more dispensing steps (box 108, as also shown in FIGS. 4A-4B) to generate the custom-formulated personalized nutritional composition, for packaging and shipping, as is shown in relation to FIGS. 4A-6.

Returning to the implementation of FIG. 3, the formulated composition is packaged via one or more packaging steps (box 110) so as to be packaged and transmitted to the delivery unit (box 112) for delivery to the subject via one or more delivery steps, as is discussed further in FIGS. 4A-6. It is understood that each of these optional steps may be performed in any order or omitted, and that additional steps may be contemplated in further implementations.

In various implementations, the formulation dictated by the dispensing instructions comprises several optional steps. In the implementation of FIGS. 4A-4B, the system 10 performs a sequence of optional steps to produce and dispense active ingredients from the actives library.

In various implementations, such as that of FIGS. 4A-4B, the dispensing unit 12 performs at least one dispensing step in response to the received dispensing instructions. It is understood that in these implementations, the dispensing unit 12 counts or otherwise weighs the active ingredients according to the received dispensing instruction. It is understood that based on which of the one or more actives that are identified by foregoing processes, a custom formulation is determined to optimize the delivery of the actives. In certain implementations, the custom formulation is comprised of one or more formulation parameters. Formulation parameters include, but are not limited to: per dose of active; vehicle; excipient; dosage form (e.g. tablet, gel capsule, minibeads); flavoring, and granulation.

As shown in the implementations of FIGS. 4A-4B, the dispensing unit 12 may have one or more active vessels 40 constructed and arranged to house one or more active ingredient(s), wherein each of the plurality of active vessels is configured to dispense a quantity of the active ingredient determined by the dispensing instructions. In the implementations of FIGS. 4A-4B, the active vessels 40 are modular counting machines 40A, 40B constructed and arranged such that the dispensing instruction is translated and executed so as to count out, combine, weigh and/or otherwise batch raw materials—such as active(s) and/or any vehicle(s) via a PLC or other processor in operational communication with the dispensing unit 12. Other active vessels are of course possible, as would be readily apparent to one of skill in the art.

In certain implementations, the modular counting machine(s) 40A, 40B are constructed and arranged to dispense materials into a mixing chamber 42 for further processing according to the disclosed implementations. In one optional system 100 step, the system performs a weighing step as part of dispensing. During the weighing step, in response to a received dispensing instruction, the dispensing unit 12 selects and accurately weighs active ingredient(s) and/or any vehicle(s) for dispensing into the mixing chamber.

It is appreciated that in certain of these implementations, and as shown in FIG. 4A and FIG. 4B, the mixing chamber 42 or containers may be disposed on a conveyor belt 22 for transport to the feed opening 44 in the bagging unit 14.

In various implementations, the modular counting machine(s) 40A, 40B are constructed and arranged to support a quick change system. In certain implementations, the modular counting machine(s) 40A, 40B are also constructed and arranged to support human-computer interaction. Further implementations are of course possible.

Figure 5:
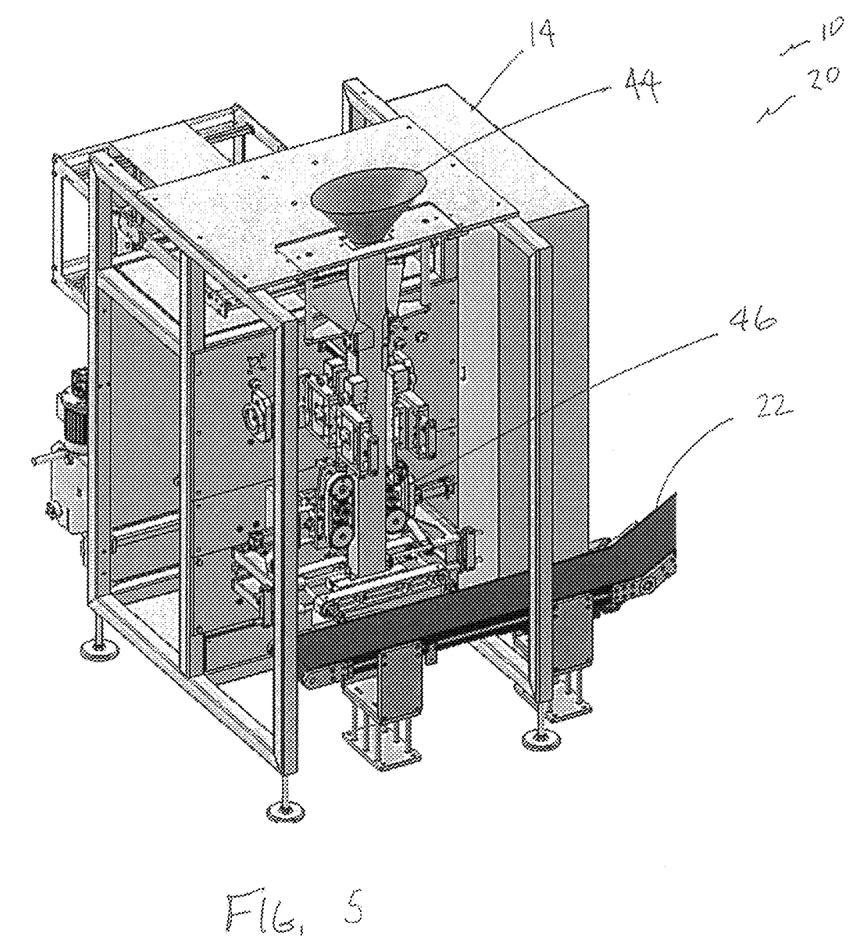
FIG. 5 is a perspective internal view of a bagging unit, according to one implementation.

As shown in the implementations of FIGS., the system 10 having a packaging unit 11 may execute a bagging step via a bagging unit 14, shown in detail in FIG. 5. In these implementations, the active(s) or other compositions are introduced into the feed opening 44 for individual bagging via a bagging mechanism 46 via the mixing chamber 42.

Figure 6:
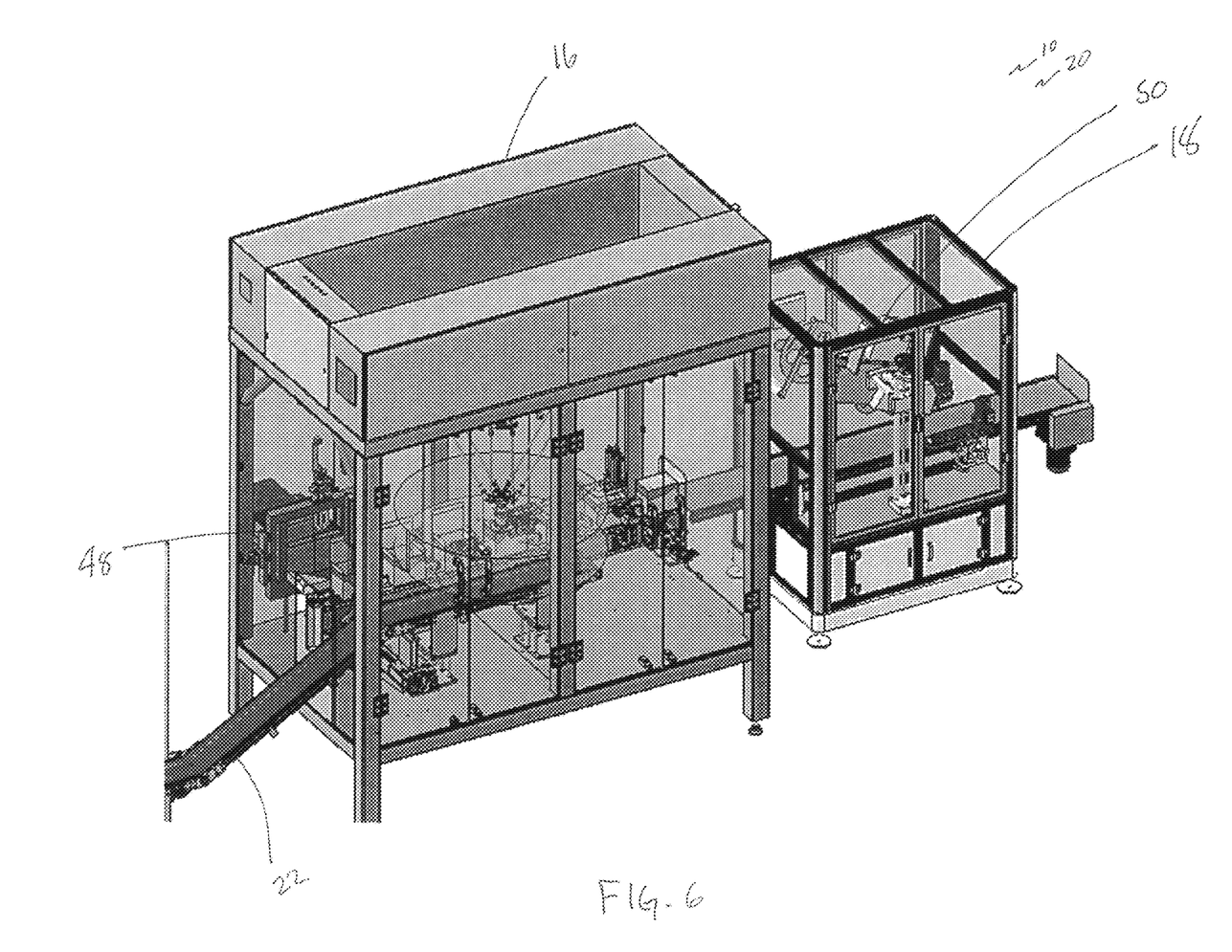
FIG. 6 is a perspective view of a boxing unit and delivery unit, according to one implementation.

In another optional step, the bagged units are transported to a boxing unit 16 for boxing via a boxing mechanism 48 and then on to a delivery unit 18 for the application of personalized labels, such as shipping labels, via a labeling mechanism 50 for subsequent transport via the shipping unit. It is understood that the labeling mechanism can label or otherwise mark the package with shipping information including an address and carrier, including pre-paid shipping information or labels. It is further understood that in various implementations, the delivery unit 18 can be constructed and arranged to affix labels and outboard units for shipping, as would be understood.

In various implementations, the system 10 comprises a power supply and computing components, such as a microprocessor, memory and the like. In additional implementations, computing and other processing is done within each module. In certain implementations, a variety of program modules are configured to execute a series of optional steps relating to the execution of the described processes. In various implementations, the system executes a series of optional algorithmic steps.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example I

Subject A, age 55 years old, male, in general good health, takes a diagnostic blood testing to assess nutrient levels under a health care provider's care. The nutrient levels assessed include: antioxidants; B-vitamins; minerals; essential fatty acids; digestive support; vitamin D; and amino acids.

The healthcare provider analyzes testing results and inputs values into the software module. The health care provider determines subject severely lacking in levels of alpha lipoic acid and also in need of certain B vitamins and minerals. The software module presents the healthcare provider with potentially relevant actives from the actives library. The healthcare provider selects the appropriate actives and the appropriate dose for each active. The software's interface allows the physician to upload the testing results from the lab. The healthcare provider inputs the following prescription information into the software module: Prescription for subject A, once a day for 60 days:

200 mg alpha lipoic acid
25 mg Thiamin (B1)
25 mg Pyridoxine (B6)
5 mg Manganese The software module (shown in FIG. 1 and FIG. 2 at 30) analyzes the prescription information and generates dispensing instructions to send to the batching and delivery components (shown a in FIG. 1 and FIG. 2 at 20)/dispensing unit (shown in FIG. 1 and FIG. 2 at 12). The dispensing unit receives dispensing instructions from the software module and dispenses each of the actives from the active vessels at the precise amount in the form of minibeads (in minibead, minitab, and minidrop form) by counting the numbers for each minibead.

| Health Care Provider Input Dose | Dispensing Unit Output |
|---|---|
| Alpha lipoic acid (200 mg) | 15 minibeads |
| Thiamin B1 (25 mg) | 2 minibeads |
| Pyridoxine B6 (25 mg) | 2 minibeads |
| Manganese (5 mg) | 2 minibeads |
| Total | 21 minibeads |

The minibeads for each active are then transported via a conveyer belt (shown, for example in FIG. 1 at 22) to the mixing chamber (shown above at 42) and combined into a nutraceutical product. The combined minibeads are sent to the packaging unit (shown in FIGS. 1-3 at 11), to package the nutraceutical product into daily doses. A Supplement Fact label will be generated from the labeling software.

A total of 60 packages (each representing a single daily dose) are then boxed and transported to the delivery unit (shown in FIG. 1 at 18). The delivery unit receives delivery instructions from the software module and delivers the packaged nutraceutical product to the subject.

The subject's physician continues to monitor the progress of the subject, and at two months' time, another diagnostic testing will be prescribed and a new prescription may be prescribed based on the progress of the subject. A new personalized nutraceuticals will be manufactured and delivered according to the updated health information.

Example II

In exemplary embodiments, a formula for bone health is comprised of the actives: vitamin D, magnesium, zinc, vitamin k2, an anti-inflammatory agent and a small amount of calcium citrate. The user (e.g., heath care provider) adjusts formula by way of the software module to optimize vitamin D level accounting for the amount in the subject's multivitamin. If the subject has health conditions requiring the avoidance of zinc (e.g., they are on AREDS macular degeneration formula and are already getting 80 mg) the user can indicate such a condition via the software module and zinc will be omitted. In certain implementations, vitamin D level are assessed by the subject via home lab testing or via a health care provider. In the event that levels are found to be low, that information in entered into the software module for subsequent vitamin D dose increase. The software module will then prompt the user in enter new values within 1-2 months to reassess the modified does.

Although the disclosure has been described with reference to preferred embodiments, persons skilled in the art will recognize that changes may be made in form and detail without departing from the spirit and scope of the disclosed apparatus, systems and methods.

What is claimed is:

1. A system to deliver personalized and precision nutraceutical products to a subject, comprising:
   a) a library of actives comprising a plurality of nutraceutical active ingredients, wherein each of the plurality of nutraceutical active ingredients is comprised of a plurality of minibeads, and wherein each of the plurality of minibeads has a size ranging from about 0.5 mm to about 10 mm in diameter and/or length;
   b) a software module; and
   c) a dispensing unit, wherein the one or more actives is precisely dispensed by counting the number(s) of minibeads, of each of the one or more actives.

2. The system of claim 1, further comprising a packaging unit and a delivery unit.

3. The system of claim 1, wherein the plurality of active nutraceutical ingredients are formulated for precise dispensing.

4. The system of claim 1, wherein the software module is constructed and arranged to receive prescription information for the subject and to output dispensing instructions to the dispensing unit.

5. The system of claim 1, wherein the dispensing unit is constructed and arranged to receive dispensing instructions from the software module and to dispense one or more actives from the library of actives to form a nutraceutical product, and wherein the dispensing instructions are derived from the prescription information and customized to the nutritional needs of the subject.

6. The system of claim 2, wherein the packaging unit is constructed and arranged to package the nutraceutical product and wherein the nutraceutical product is packaged in sachets, bottles, jars, tubes, canisters, drums, boxes, or cases.

7. The system of claim 2, wherein the delivery unit is constructed and arranged receive delivery information from the software module and to deliver the packaged nutraceutical product to the subject.

8. The system of claim 1, wherein the nutraceutical actives are one or more of vitamins, minerals, amino acids, herbs, botanicals, enzymes, probiotics, prebiotics, or a concentrate, metabolite, constituent, extract or combination of any of the foregoing and wherein the nutraceutical product is formulated for a specified health condition or nutritional need.

9. A system for dispensing a personalized nutraceutical product to a subject comprising:
   a) a software module constructed and arranged to receive prescription information from the subject's healthcare provider;
   b) a library of actives, comprised of a plurality of nutraceutical active ingredients, wherein each of the plurality of nutraceutical active ingredients is comprised of a plurality of minibeads and wherein each of the plurality of minibeads has a size ranging from about 0.5 mm to about 10 mm in diameter and/or length;
   c) a dispensing unit constructed and arranged to receive dispensing instructions from the software module and to precisely dispense one or more active ingredients from the library of actives, the dispensing unit comprising:
      i) a plurality of active vessels, wherein each of the plurality of active vessels houses a single active ingredient, wherein each of the plurality of active vessels is configured to dispense a quantity of the active ingredient determined by the dispensing instructions, wherein the quantity of each active ingredient dispensed is precisely determined according the number of the minibeads dispensed;
      ii) a dispensing belt, positioned below the plurality of active vessels and configured to received one or more active ingredients dispensed from the active vessels; and
      iii) a mixing chamber, constructed and arranged to receive one or more actives from the dispensing belt and to mix the one or more active ingredients to form a nutraceutical product;
   d) a packaging unit, constructed and arranged to package to the nutraceutical product; and
   e) a delivery unit, constructed and arranged to receive delivery instructions from the software module and deliver the packaged nutraceutical product to the subject.

10. The system of claim 9, wherein the software module provides an interface for the healthcare provider to input dosage levels for each of the one or more active ingredients.

11. The system of claim 9, wherein the nutraceutical active ingredients are vitamins, minerals, amino acids, herbs, botanicals, enzymes, probiotics, prebiotics, or a concentrate, metabolites, constituent, extract or combination of any of the foregoing.

12. A method of delivering a nutraceutical product to a subject in need thereof comprising:
   a) receiving prescription information from a healthcare provider of the subject via a software module;
   b) inputting dispensing instructions from the software module into a dispensing unit, wherein the dispensing unit is comprised of a plurality of active ingredient vessels, and wherein each of the active ingredient vessels houses one of a plurality of nutraceutical active ingredients and wherein each of the plurality of nutraceutical active ingredients is comprised of a plurality of minibeads and wherein each of the plurality of minibeads has a size ranging from about 0.5 mm to about 10 mm in diameter and/or length;
   c) dispensing a precise quantity of the one or more of the active ingredients from the active vessels according to the dispensing instructions, wherein the one or more actives is precisely dispensed by counting the number (s) of minibeads, of each of the one or more actives;
   d) mixing the one or more active ingredients in a mixing chamber to form a nutraceutical product; and
   e) packaging to the nutraceutical product for delivery to the subject.

13. The method of claim 12, wherein the nutraceutical active ingredients are vitamins, minerals, amino acids, herbs, botanicals, enzymes, probiotics, prebiotics, or a concentrate, metabolites, constituent, extract or combination of any of the foregoing.

14. The method of claim 12, wherein the product is packaged in sachets, bottles, jars, tubes, canisters, drums, boxes, or cases.

* * * * *